US00PP26644P2

(12) United States Plant Patent
Bedford et al.

(10) Patent No.: US PP26,644 P2
(45) Date of Patent: Apr. 26, 2016

(54) APPLE TREE NAMED 'MINNB42'

(50) Latin Name: *Malus domestica*
Varietal Denomination: MINNB42

(71) Applicants: David Bedford, New Germany, MN (US); James Luby, St. Paul, MN (US)

(72) Inventors: David Bedford, New Germany, MN (US); James Luby, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 150 days.

(21) Appl. No.: 13/999,415

(22) Filed: Feb. 24, 2014

Related U.S. Application Data

(60) Provisional application No. 61/851,785, filed on Mar. 13, 2013.

(51) Int. Cl.
*A01H 5/08* (2006.01)

(52) U.S. Cl.
USPC ..... Plt./161

(58) Field of Classification Search
USPC ..... Plt./161
See application file for complete search history.

*Primary Examiner* — June Hwu
(74) *Attorney, Agent, or Firm* — Penny J. Aguirre

(57) ABSTRACT

A new cultivar of apple tree, 'MINNB42', that is characterized by its fruit that is distinct in its ability to develop deeply colored red fruit skin in climates (such as southern Pennsylvania and southern New York) that are not conducive to producing well-colored 'Honeycrisp' fruit, its fruit with a diameter of 7 to 8.4 cm, its fruit with a texture that is very crisp when eaten, its fruit with skin that is relatively thin and easy to penetrate when eaten, its fruit with a flavor that is sub-acid, its moderate tree growth rate, and its cold hardness in U.S.D.A. Zone 4.

2 Drawing Sheets

Botanical classification: *Malus domestica.*
Varietal denomination: 'MINNB42'.

BACKGROUND OF THE INVENTION

The present invention relates to a new and distinct cultivar of apple tree, botanically known as *Malus domestica* 'MINNB42', referred to hereafter by its cultivar name, 'MINNB42'.

'MINNB42' was discovered by the Inventors in 1999 as a naturally occurring branch mutation of 'Honeycrisp' (U.S. Plant Pat. No. 7,197). The branch mutation was discovered on a 'Honeycrisp' tree 16 in row 3 of block 42 at a research center in Excelsior, Minn. The new cultivar was given the reference No. B42-3-16A for testing and trial purposes.

Asexual propagation of the new cultivar was first accomplished by budding onto clonal rootstock in 2001 under the direction of the Inventors in Excelsior, Minn. Further asexual propagation by budding onto clonal rootstock and observation of the resulting trees in Excelsior, Minn.; Highland, N.Y. and Biglerville, Pa. has determined that the characteristic of the new cultivar are stable and are reproduced true to type in successive generations.

SUMMARY OF THE INVENTION

1. The following traits have been repeatedly observed and represent the characteristics of the new cultivar and distinguish 'MINNB42' as a unique cultivar of apple tree. The characteristics of 'MINNB42' were tested in replicate trials in Excelsior, Minn.; Highland, N.Y., and Biglerville, Pa. for periods ranging from 5 to 14 years
2. 'MINNB42' exhibits fruit that is distinct in its ability to develop deeply colored red fruit skin in climates (such as southern Pennsylvania and southern New York) that are not conducive to producing well-colored 'Honeycrisp' fruit. These observations have been confirmed through analytical evaluations performed over multiple years (as described below and shown in TABLE 1).
3. 'MINNB42' exhibits fruit with a diameter of 7 to 8.4 cm.
4. 'MINNB42' exhibits fruit with a texture that is very crisp when eaten.
5. 'MINNB42' exhibits fruit with skin that is relatively thin and easy to penetrate when eaten.
6. 'MINNB42' exhibits fruit with a flavor that is sub-acid.
7. 'MINNB42' trees exhibit a moderate growth rate.
8. 'MINNB42' is cold hardy in U.S.D.A. Zone 4.

'MINNB42' can be most closely compared to its parent cultivar, 'Honeycrisp'. 'MINNB42' differs most significantly from 'Honeycrisp' in its ability to produce fruit with a greater amount of red skin coloration as well a greater degree of red intensity. 'MINNB42' can also be compared to the cultivars 'Minneiska' (U.S. Plant Pat. No. 18,812), and 'Minnewashta' (U.S. Plant Pat. No. 11,367), 'MINNB42' differs from 'Minneiska' in being more resistant to apple scab and in having fruit that ripens 2 to 3 weeks later and fruit that is less conical in shape, has fewer prominent lenticels, lower acidity, a longer storage life (6 to 7 months vs. 3 to 4 months), and less prone to russeting. 'MINNB42' differs from 'Minnewashta' in being more resistant to apple scab, in having a less vigorous growth habit, in blooming later, and in having fruit that ripens about 3 weeks later, has flesh that is crisper and less prone to oxidative browning when exposed to air, and in having fruit with a longer storage life (6 to 7 months vs. 7 weeks).

FRUIT COLOR EVALUATIONS OF 'MINNB42'

For the evaluations, 'MINNB42' is stated as its reference No. B42-3-16A, and 'Honeycrisp' is stated as its reference no. S-11-E.

In 2006 ten strains of different 'Honeycrisp' selections were grafted onto third leaf 'York Imperial'/Bud.9 trees at a research center in Biglerville, Pa. with the intention of verifying the fruit color determinations from a previous trial, with advanced colorimetric, photometric, and image analysis techniques. Another goal was to determine whether these strains offered an improvement in fruit appearance in terms of increased intensity of red color and increased blush coverage in southern Pennsylvania. A total of 495 trees were topworked with the strains in a replicated, randomized fashion.

For the years 2008 and 2009 blush coverage was estimated using visual inspection of replicates of 25 fruits per replicate. In 2009, 2010 and 2011, a digital image analysis technique was used. This process involved taking photographs of apples in a standard light box, calibrating photographic output using reference color chips, and using JAVA software to iteratively classify each pixel in each image as non-apple, blush, or non-blush (Winzeler and Schupp, 2011).

Analysis of blush color intensity was accomplished through colorimetry, using a KONICA MINOLTA spectrophotometer model CM-2600d (Konica Minolta Sensing Inc., Osaka, Japan). Colorimetry was referenced to the CIE $L^*C^*_{ab}h_{ab}$ color space of the International Commission on Illumination, where L* represents the lightness of the color, $C_{ab}^*$ represents the chroma or saturation intensity, and $h_{ab}$ represents hue, or the angular component of the polar representation of CIELAB color space (CIE, 1978). Each apple in each replicate was analyzed with a spectral measurement on the blush side and another on the background side.

The anthocyanin index, modified from Merzlyak et al. (2003), is a non-destructive estimator of anthocyanin content using spectral response of a pulsed xenon light at specific wavelengths absorbed or reflected by anthocyanin. This index was applied to spectral data from the CM-2600d to help quantify the relative anthocyanin content and the resulting intensity of red color in apple samples.

The results of the color evaluation between B42-3-16A ('MINNB42'), and S-11-E ('Honeycrisp') are shown in TABLE 1. In 2009, B42-3-16A had a lower hue angle (was redder) and had a greater percentage of blush coverage than S-11-E (Table 1). In 2010 and 2011, B42-3-16A had a darker and redder color on the blush side of the fruit and had more extensive blush coverage than S-11-E. Blush coverage measurements from 2009, 2010 and 2011 were analyzed with digital image analysis according to Winzeler and Schupp (2011), eliminating the possibility of subjectivity in color rating. Representative images of the fruits are shown in FIG. 2. In 2010 and 2011, the B42-3-16A fruit displayed higher anthocyanin index values than the standard S-11-E on the blushed side of the fruit (anthocyanin values were not recorded in 2009).

REFERENCES

C.I.E. 1978. Recommendations on uniform color spaces, color difference equations, and metric color terms. Suppl. No. 2 to Pub. No. 15, Paris, France.

Merzlyak, M. N., A. E. Solovchenko, and A. A. Gitelson. 2003. Reflectance spectral features and non-destructive estimation of chlorophyll, carotenoid and anthocyanin content in apple fruit. Postharvest Biology and Technology 27: 197-211.

Winzeler, H. E. and J. R. Schupp. 2011. Image analysis of blush coverage extent and measures of categorical blush intensity in 'Honeycrisp' apples. HortScience 46(5): 705-709.

BRIEF DESCRIPTION OF THE DRAWINGS

The accompanying color photographs were taken of fruit harvested from trees of 'MINNB42' that were grown in a trial plot for approximately 6 years in Biglerville, Pa. The colors in the photographs are as close as possible with the photographic and printing technology utilized and the color values cited in the detailed botanical description accurately describe the colors of the new apple tree. The photograph in FIG. 1 provides a view of the fruit of 'MINNB42' (Labeled as Ref No. B42-3-16A).

The photograph in FIG. 2 provides a view of fruit of 'Honeycrisp' (Ref. No. S-11-E) on the top of the photograph and fruit of 'MINNB42' (Labeled as Ref No. B42-3-16A) on the bottom of the photograph.

DETAILED BOTANICAL DESCRIPTION

Figure 1:
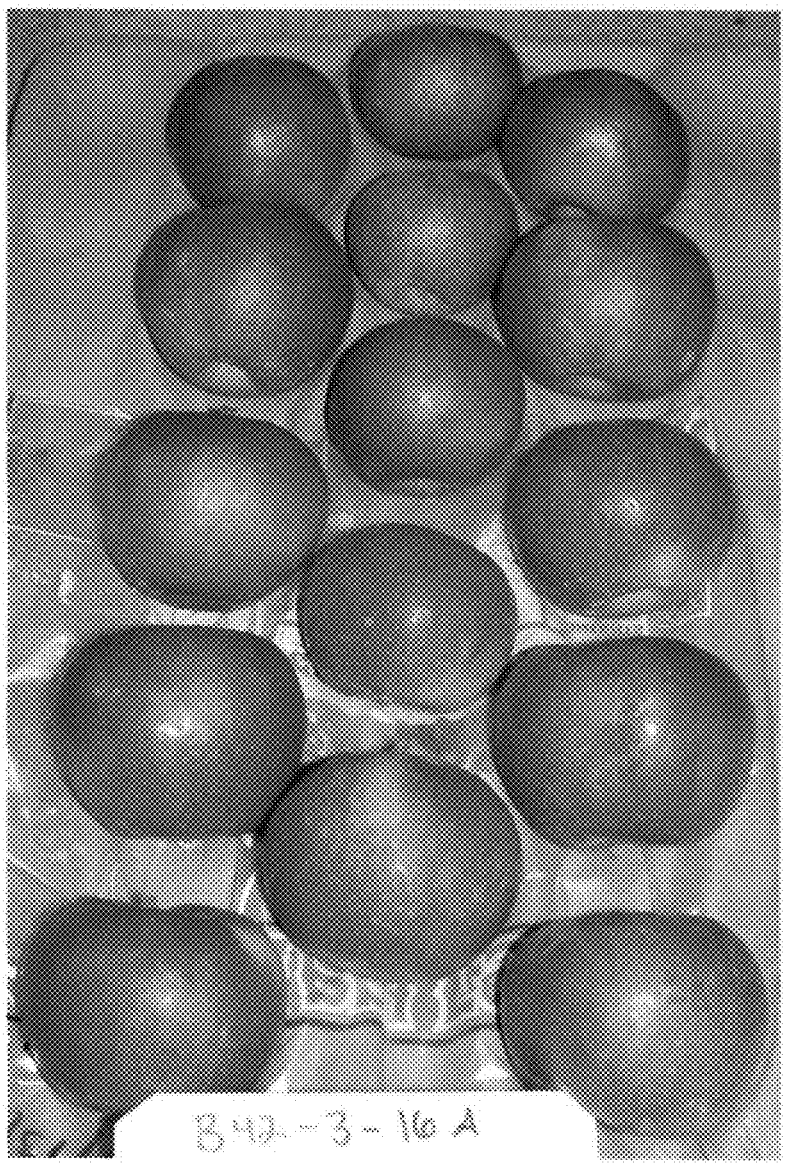
Figure 2:
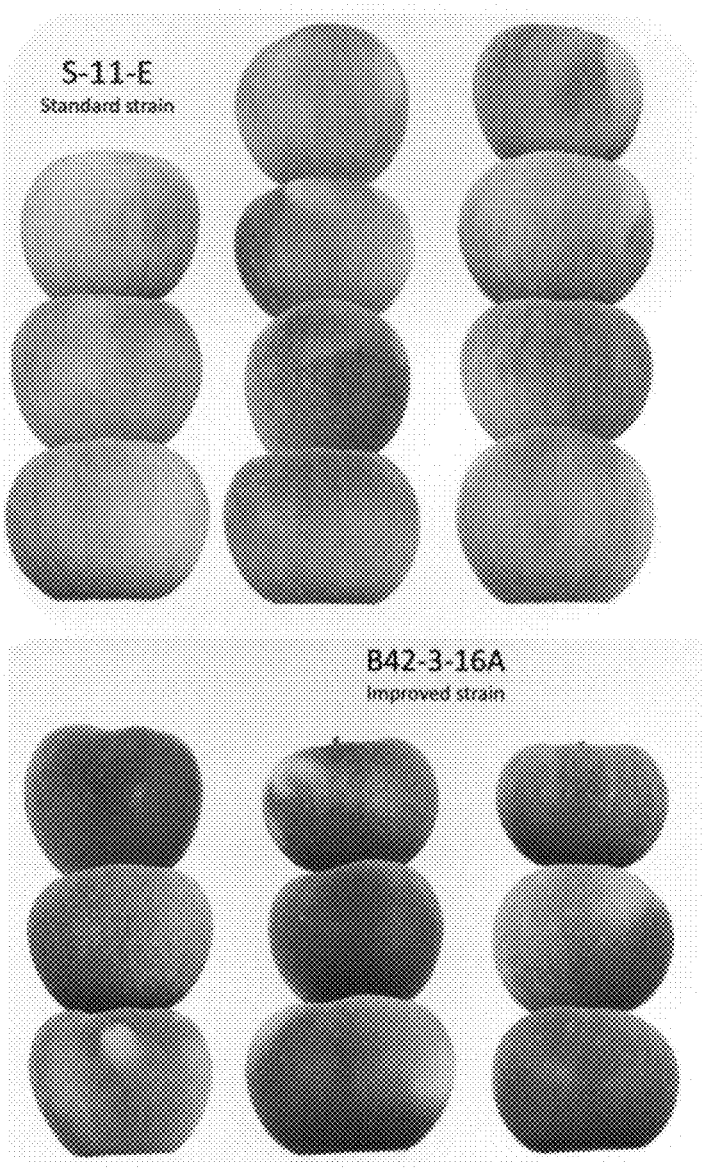

The following is a detailed description of the new apple variety as observed on plants grown for 14 years in Excelsior, Minn. Analytical data on fruit coloration was taken from fruit collected from trees grown for 4 to 6 years in Biglerville, Pa. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

Tree description:

*Habit*.—Slightly upright to spreading.

*Vigor*.—Moderate.

*Diseases resistance*.—Has shown above average resistance to apple scab on both the leaves and the fruit.

*Cold hardiness*.—U.S.D.A. Zone 4.

*Branching habit*.—Spreading.

*Branch frequency*.—Medium.

*Branch strength*.—Intermediate.

*Angle of bearing branches*.—Approximately 90°.

*Predominance of bearing*.—Both spurs and shoots.

Description of dormant shoots:

*Pubescence on upper one year-old shoot*.—Medium.

*Shine of bark*.—Weak.

*Thickness of shoot at center of middle internode*.—Average of 5.13 mm.

*Bark color* (*using bark on* 1 *year old shoots exposed to sun*).—178A.

*Shoot angle*.—Approximately 90°.

*Lenticel*.—Medium in size and number, color 159C.

Description of growing shoots:

*Color of growing tip of shoot*.—193B.

*Shape of shoot tips leaves in cross section*.—Concave.

*Pubescence of shoot tip leaves*.—Weak to medium on upper surface of leaf and dense on lower side.

*Color of shoot tip leaves*.—194C on lower surface and 196C on upper surface.

*Distribution of color other than green on shoot tips leaves*.—None.

Leaf description:

*Leaf orientation*.—Outward.

*Leaf division*.—Simple.

*Leaf shape*.—Ovate.

*Leaf size*.—Average of 9.51 cm in length and 5.2 cm in width ($4^{th}$ to $6^{th}$ leaf).

*Leaf apex*.—Cuspidate.

*Leaf base*.—Oblique or obtuse.

*Leaf surface*.—Medium glossiness on upper surface, pubescent on lower surface.

*Leaf margin*.—Crenate to serrate.

*Leaf color*.—Upper surface 147B, lower surface 148B.

*Leaf anthocyanin on lower surface*.—None.

*Leaf venation*.—Pinnate main veins with netted minor veins.

*Petiole size*.—Average of 2.67 cm in length and 1.47 in diameter.

*Petiole color*.—145B with a tinge of anthocyanin at base 184C.

*Stipules*.—Small to medium in size (mean 0.6 cm in length), found on actively growing shoots where they are present on newly developed leaves but sometimes abscising on older leaves.

Flower description:

*Flowering period*.—Average dates: May 8th-15th (same as 'Honeycrisp') in Excelsior, Minn.

*Beginning flowering date*.—Typically about May $8^{th}$, similar to 'Honeycrisp'.

*Number of flowers*.—Average of 5.1 per spur.

*Inflorescence type*.—Corymb of rotate flowers.

*Flower buds*.—At pink tip stage; 67C in color, round to conical in shape, average of 9 mm in length and 6 mm in diameter.

*Flower size*.—Average of 3.7 cm in diameter and 1.5 cm in depth.

*Flower fragrance*.—Mild.

*Flower aspect*.—Upright.

*Petals*.—5 per flower, unfused, sometimes overlapping, ovate in shape, obtuse apex, round base, entire margin, about 1.65 cm in length and 1.14 cm in width, color of upper surface when opening and mature; 155D with tinges of 65C, color of lower surface when opening and mature; 155D with tinges of 65C (greater level of tinge than upper surface), upper and lower surface glabrous.

*Sepals*.—5, color upper surface 143D, color lower surface 143D and 181D at tip, slight to moderately pubescent surface, triangular in shape, entire margin, acute apex, fused base, average of 6.8 mm in length and 3.2 mm in width.

*Pedicel*.—181B in color on side exposed to sun and 143D in color on shaded side, average of 2.47 cm in length and 2 mm in width, glabrous surface.

*Pistil*.—Compound carpel with 5 stigmas fused at base, 1 cm in length, style is 151A in color and 8 mm in length, stigma is 153A in color, ovary is pubescent and 139D in color.

*Stamens*.—Average of 17.7, anther is oblong in shape, 11C in color and 2 mm in length, pollen is 3D in color and moderate in quantity.

*Pollination requirements*.—Self incompatible.

Fruit description:

*Fruit size*.—Medium to large, 7.0 to 8.4 cm in diameter, average of 6.4 cm in height.

*Position of maximum diameter*.—Midway between proximal and distal ends.

*Fruit shape*.—Globose to globose conical.

*Fruit symmetry*.—Mostly symmetrical.

*Fruit prominence of ribbing*.—Very weak or absent.

*Fruit aperture of eye*.—Half open to closed.

*Size of eye*.—Average of 8.9 mm.

*Persistence of calyx*.—Present.

*Length of sepal*.—Average of 4.4 mm.

*Spacing of sepals at base*.—Touching to overlapping

*Depth of eye basin*.—Average of 5.2 mm.

*Width of eye basin*.—Medium, average of 22.1 mm.

*Thickness of stalk*.—Medium, average of 3.0 mm.

*Length of stalk*.—Short to medium, average of 15.7 mm.

*Depth of stalk cavity*.—Medium, average of 12.2 mm.

*Width of stalk cavity*.—Medium, average of 23.3 mm.

*Relief of surface*.—Smooth to slightly hammered.

*Bloom of skin*.—Light.

*Waxiness of skin*.—Light.

*Thickness of skin*.—Relatively thin and easy to penetrate when eaten.

*Skin color*.—Over color is 45A, ground color is 1C.

*Presence of russet*.—Low level of presence on main body; moderately present around the stalk basin.

*Lenticels*.—Medium in number, medium in size (average of 0.5 mm), low to intermediate prominence.

*Color of flesh*.—158B.

*Distinctness of core line*.—Medium.

*Aperture of locules*.—Moderately open.

*Fruit set*.—Intermediate to good.

*Fruit maturity date*.—Average harvest date is approximately September $18^{th}$ in east central Minnesota, after 'Minnewashta' and 'Minneiska'.

*Seed*.—199C in color when dry, ovoid to somewhat deltoid in shape, an average of 8.1 mm in length and 5.1 mm in diameter.

*Browning of flesh*.—Low level, less than 'Minnewashta'.

*Firmness* (*without skin*).—Medium, 13 to 18 lbs.

*Texture of flesh*.—Very crisp; retained during storage for 6 to 7 months.

*Cropping frequency*.—Annual to sometimes biennial.

*Fruit flavor*.—Sub-acid.

*Fruit productivity*.—Average annual fruit production of 32.6 lbs. per tree (observed on 8 to 9 year-old trees grafted on Budagovski 9 rootstock in Excelsior, Minn.).

*Acidity*.—An average of 0.52 titratable acidity (malic acid equivalent).

*Brix*.—An average of 13.4°.

*Storage life*.—6 to 7 months in common stage (average temperature of 34° F.), unusually long storage life for a mid ripening season variety.

*Market use*.—Fresh Fruit (particularly suitable as a dessert apple).

It is claimed:

1. A new and distinct variety of apple tree named 'MINNB42' as herein illustrated and described.

* * * * *